US00PP14074P3

(12) United States Plant Patent
Zipperer, III

(10) Patent No.: US PP14,074 P3
(45) Date of Patent: Aug. 19, 2003

(54) GLADIOLUS PLANT NAMED 'FESTIVA'

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 09/877,575

(22) Filed: Jun. 8, 2001

(65) Prior Publication Data

US 2002/0002725 P1 Jan. 3, 2002

(30) Foreign Application Priority Data

Jun. 9, 2000 (EP) ..... 2001/0892

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed Dec. 20, 2000.
U.S. patent application Ser. No. 09/742,726, Zipperer, III, filed Dec. 20, 2000.
U.S. patent application Ser. No. 09/877,571, Zipperer, III, filed Jun. 8, 2001.
U.S. patent application Ser. No. 09/877,572, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/918,662, Zipperer, III, filed Jul. 7, 2001.
U.S. patent application Ser. No. 09/918,660, Zipperer, III, filed Jul. 7, 2001.
U.S. patent application Ser. No. 09/918,663, Zipperer, III, filed Jul. 7, 2001.
Hits on UPOV–Rom Plant Variety Database, GTI Jouve Retrieval Software, 2002/03.*

* cited by examiner

*Primary Examiner*—Bruce R. Campell
*Assistant Examiner*—Anne Marie Grünberg
(74) *Attorney, Agent, or Firm*—Han , Loeser & Parks LLP; Laura G. Barrow

(57) ABSTRACT

A new and distinct gladiolus variety, designated 'Festiva', is shown and described. Compared to the 'Jennie Lee' parent variety, 'Festiva' has a similar bloom diameter, produces stems having the same length, but produces one to two less florets per stem.

4 Drawing Sheets

The present invention comprises a new and distinct variety of a *Gladiolus l.* referred to by the variety name 'Festiva.'

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed. (The provisional breeder's designation "28-3" was used in a related application for a Community plant variety right filed earlier in the European Union Community Plant Variety Office). The female parent was an unpatented gladiolus variety named 'Dr. Magie,' characterized in part by having a small pink bloom, a short stem having a short flower head, and high resistance to Fusarium fungi species. The male parent was a salmon pink gladiolus variety named 'Jennie Lee,' an unpatented, released variety (by Jennie Lee Zipperer), characterized in part by having a long stem, long head, and high floret count (i.e. 18–20 florets) when grown from a jumbo bulb (i.e. 1.75 inches and larger) in south Florida. The seeds were planted in Ft. Myers, Fla., and the selection of the 'Festiva' variety was made in Spring 1988. Asexual reproduction of the 'Festiva' variety was achieved by collecting cormels from the first corm and growing said cormels to maturity in Ft. Myers. All subsequent asexual reproductions of the 'Festiva' variety remain true to the original variety type.

BONTANICAL DESCRIPTION

Figure 1:
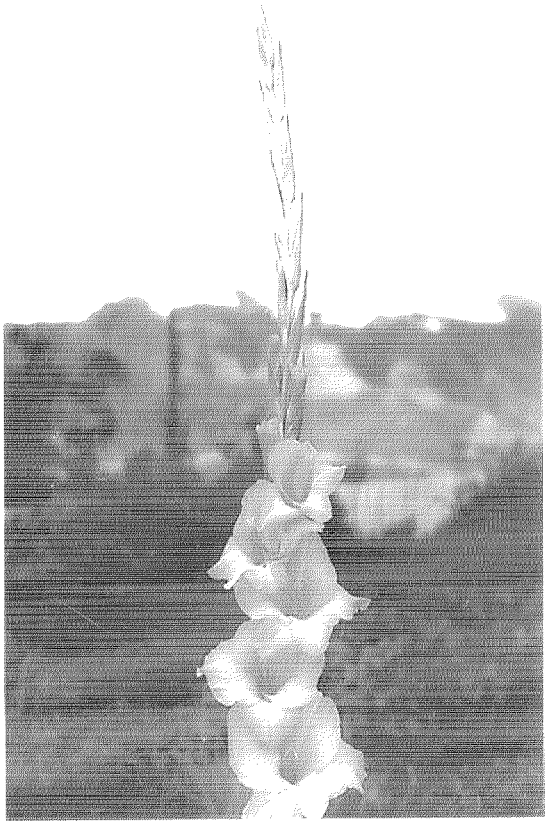
FIG. 1 is a photograph of a 'Festiva' variety plant in bloom.
Figure 2:
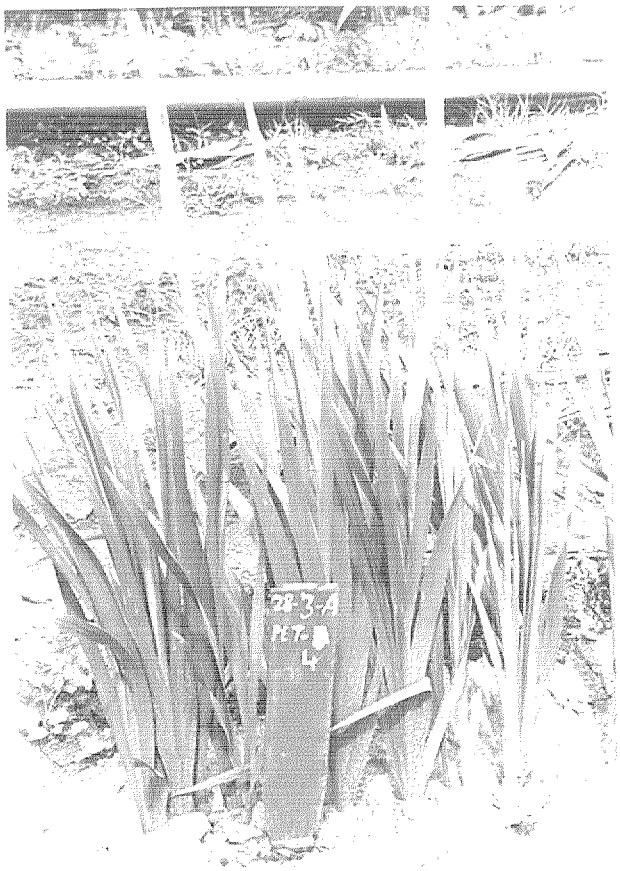
FIGS. 2 and 3 are photographs of the 'Festiva' variety plant prior to blooming.
Figure 3:
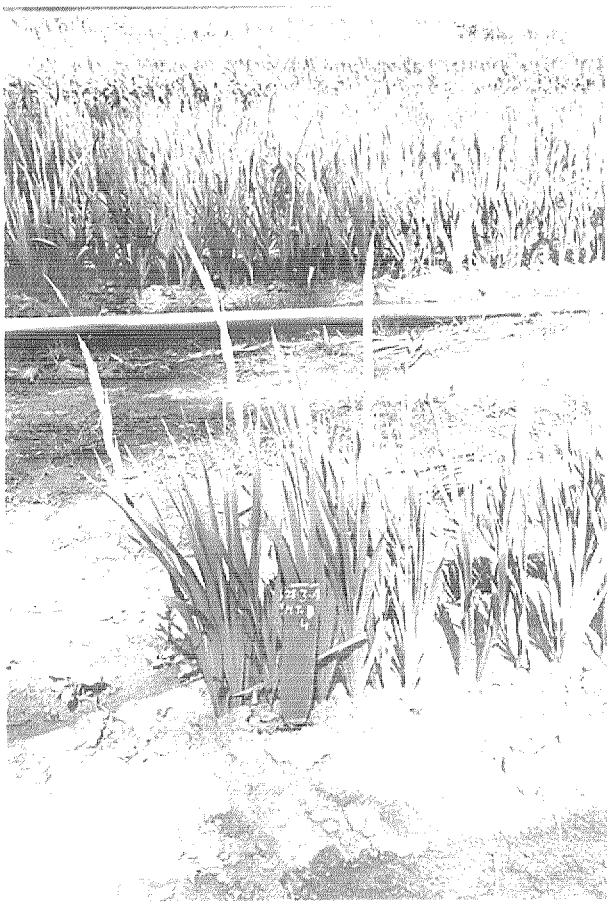
Figure 4:
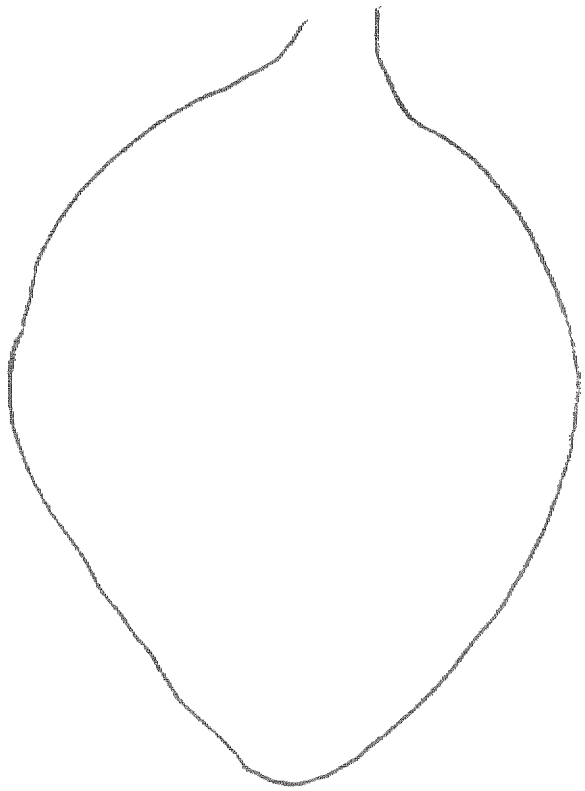
FIG. 4 is a drawing illustrating the shape and size of the large petals.

The accompanying color photograph (FIG. 1) shows the inflorescence and various stages of blooming of the 'Festiva' variety plant.

The following botanical description, except for color, of the 'Festiva' variety was observed when the plant was 90 days old grown under the following conditions in Ecuador:

1) Twelve-hour daylight days with high light intensity.

2) Temperatures: 58–60° F. (low's) and 69–75° F. (high's).

3) Humidity: 50–55%.

4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 118 cm and comprises 17 florets when grown from #2 size corms (1.25 to 1.50 inches) in Ecuador. The color of the spike is Yellow Green Group 144D. The head length is 48 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes).

The leaf color of the 'Festiva' variety is Green Group 137C on both sides. The leaf size is about 63 cm (length) by 3.5 cm (width).

The bud size of the 'Festiva' variety is about 7.5 cm in length. The flowers of the variety each consist of a total of six petals. Specifically, in one arrangement, each bloom consists of one large petal oriented on the top part of the bloom near 12:00 (referring to the face of clock), one small-sized petal oriented on the lower half of the bloom (at about 6:00), and four medium-size petals also oriented on the lower part of the bloom. The most common petal arrangement consists of three large petals located in the upper half of the bloom (between 9:00 and 3:00), one medium-size petal located in the lower half of the bloom, and two small petals also positioned in the lower half of the bloom. The diameter of the entire bloom is about 13 cm.

The color of the corolla bloom is Yellow Group 4D deep within the throat of the bloom, followed by Red Group 52C. The yellow color is observed on the inner part of the medium and small petals, and the medium petals also have a splash of White Group 155B in the center of the petal, followed by Red Group 52C. All six petals have a line (White Group 155B) bisecting the petal lengthwise. The color of the bloom tight is Red Group 49B. The color of the bloom open perfect condition is Red Group 52C. The color of the bloom open going down is Red Group 52D.

The variety has three stamens and one pistil. The color of the pistil stem and tips is White Group N155B. The color of the pistil head is Red Purple Group 62B. The color of the stamen head is Red Purple Group 64B, and the color the stamen stem is White Group N155A.

The corms of the 'Festiva' variety are typical for the gladiolus and have a Yellow-Orange Group 23A color under the husk on the top of the bulb one day after harvest.

GENERAL OBSERVATIONS

Compared to the parent 'Dr. Magie,' the 'Festiva' variety produces stems that are about 25 cm taller, has three to four more florets per stem, and a bloom diameter that is 2–3 cm larger. The variety is also less resistant to Fusarium compared to 'Dr. Magie.' When compared to the parent 'Jennie Lee,' the most similar variety to 'Festiva,' the 'Festiva' variety produces stems of the same length, one to two florets less per stem, and a similar bloom diameter. In addition, the 'Festiva' variety takes seven more days to begin harvesting after planting (i.e. nearly 90 days) compared to 'Jennie Lee.' The 'Festiva' variety has performed well when grown during fall, winter, and spring months in Ecuador. Growth is good during short days as well as in cold weather. The variety shows good resistance to burning in hot weather.

The variety opens well after traveling up to seven days in a dry box, and can hold up to six florets open simultaneously in a vase of water. The variety takes about two days to open the first bloom, which lasts for 2.5 days. The total duration of blooming is nine days from the day the plant is placed in water.

The variety does not emit a fragrance.

I claim:

1. A new and distinct gladiolus variety of plant, 'Festiva', as shown and described herein.

* * * * *